United States Patent [19]

Beisang, III et al.

[11] Patent Number: 4,596,250
[45] Date of Patent: Jun. 24, 1986

[54] MOLDABLE COOLING/HEATING DEVICE WITH DIRECTIONAL COOLING/HEATING

[75] Inventors: Arthur A. Beisang, III, Little Canada, Minn.; Robert A. Ersek, Austin, Tex.; Arthur A. Beisang, Roseville, Minn.

[73] Assignee: Genetic Laboratories, Inc., St. Paul, Minn.

[21] Appl. No.: 671,410

[22] Filed: Nov. 14, 1984

[51] Int. Cl.4 .......................... A61F 7/08; A61F 7/10
[52] U.S. Cl. ..................... 128/402; 62/530; 128/403
[58] Field of Search ............... 128/402, 403, 401; 62/530; 220/3.1

[56] References Cited

U.S. PATENT DOCUMENTS

| | | | |
|---|---|---|---|
| 3,463,161 | 8/1969 | Andrassy | 128/403 X |
| 3,545,230 | 12/1970 | Morse | 128/403 X |
| 3,736,769 | 6/1973 | Petersen | 52/530 |
| 3,951,127 | 4/1976 | Watson et al. | 128/403 X |
| 4,074,717 | 2/1978 | Schulze | 128/303.1 |
| 4,154,245 | 5/1979 | Daily | 128/402 X |
| 4,404,820 | 9/1983 | Romaine | 62/530 |
| 4,457,308 | 7/1984 | Golke et al. | 128/399 |

*Primary Examiner*—Anton O. Oechsle
*Attorney, Agent, or Firm*—Orrin M. Haugen; Thomas J. Nikolai

[57] ABSTRACT

A temperature control device containing a mixture of de-ionized water, propylene glycol, polysaccharides and plant gum for providing a moldable pillow-like surface for cooling/heating and positioning body organs or parts. A multi-layered container including an insulator, a radiant heat reflecting layer and a liquid impermeable outer layer permit autoclaving and provide directional cooling/heating. The inclusion of appropriate phase change chemicals or reciprocal iontype chemicals or metal particles facilitate the stabilization of temperature over a predetermined temperature range.

11 Claims, 4 Drawing Figures

MOLDABLE COOLING/HEATING DEVICE WITH DIRECTIONAL COOLING/HEATING

BACKGROUND OF THE INVENTION

I. Field of the Invention

This invention relates generally to a cooling or heating device and more particularly, to a moldable, autoclavable device with directional temperature control properties for cooling body organs and parts during surgery or transporting or alternatively heating body parts, such as the ankle, elbow or hands, etc.

II. Discussion of the Prior Art

During many medical procedures, such as open heart surgery, bypass surgery, kidney surgery, surgery of the pancreas, radio or chemotherapy, etc., it is desirable to reduce the temperature of the subject organ so as to slow the metabolic processes thereof during the procedure. The trauma to the organ due to the procedure is thus reduced and the medical professional is also provided additional time to complete the procedure. While the advantages of cryomedicine have been known, the application to many of the foregoing procedures has been hampered by the unavailability of a suitable device which can be used to facilitate organ cooling, but which does not cause damage to the tissue because of overcooling and which does not cause undue cooling of other proximately located body parts. Further, because of the varying organ shapes, it is not only desirable, but necessary, that any such device be moldable so as to conform to the organ's shape and to provide cooling to as large a surface area as possible.

Heretofore, a variety of cold pack devices have been developed for a variety of other applications. These typically have been based upon the principle of an icepack or a frozen water-alcohol mixture contained within a water impermeable container and intended to be held against the object to be cooled. A readily apparent problem with such devices is that when frozen, they solidify and thus do not provide a soft, deformable cooling surface. Above the freezing temperature, they merely act as liquid filled flexible bags that do not hold a shape other than that assumed by the bag when it is placed or held on a surface. The actual cooling area thereby depending upon the weight of the object cooled or the force applied in holding it.

A major drawback of prior art cold packs, therefore, is that they do not permit a shaping of the cold pack so as to maintain a a stable, yet pliable, profile at the temperatures desired for most surgical procedures, e.g. temperatures in range of from 0° C. to −17° C. Another drawback is that they tend to absorb heat rapidly and consequently require frequent replacement. Accordingly, the present invention has been designed to remain moldable and provide cooling for a relatively long period of time, even when placed in relatively warm surroundings. It has also been designed to be capable of being autoclaved. Still further, it has been designed to permit its use as a heating pack.

Examples of some cold pack devices which go beyond a simple icepack can be seen in U.S. Pat. Nos. 3,545,230; 3,736,769; and 4,457,308. The device disclosed in the U.S. Pat. No. 3,545,230 comprises a hydrophilic gel which is coated on a flexible substrate and the substrate retains its flexibility even when frozen. The U.S. Pat. No. 3,736,769 discloses a multi-layered device also containing a core of hydrophilic, alginate containing gel coated layers contained within a polyethylene envelope and having upper and lower walls of different thermal conductivities. The U.S. Pat. No. 4,457,308 describes a liquid nitrogen cooled cushion containing a silica gel and which gel combines with the liquid nitrogen to provide a deformable cushion. None of the cold packs disclosed, however, are useable as heating packs.

SUMMARY OF THE INVENTION

While the above-mentioned patents disclose various deformable cold packs, they are not constructed to permit their alternative use as a heat pack. The present invention, on the other hand, provides for a sterilizable, moldable cold pack using a dough-like temperature storage medium in a packaging arrangement that provides surfaces of differing thermal conductivities and heat reflecting properties so as to prolong the useful cooling/heating time thereof. It does so in a construction that permits the molding of its shape and the retention thereof throughout a surgical procedure.

In various of its embodiments, the temperature storage medium comprises a mixture of water, propylene glycol and various polysaccharides and plant gums. In other embodiments, the addition of desirable phase change materials, reciprocal ion pair materials and/or stainless steel or other metal or specific heat particles extend the usable cooling time.

The cold pack container comprises a multi-layered container filled with the above cooling medium. These materials remain plastic for temperatures in the range of −17° C. to 140° C. The container, includes a radiant heat-reflecting film over various portions thereof, and an insulator over the same or other portions and which together facilitate directional cooling. The container and its contents are also designed to be compatible with autoclaving. Because of the compatibility of the present cold pack to heat, it also may be used as an efficient directional moldable heating pack and will, accordingly, be referred to hereinafter as a cold/heat pack. Still further, the design allows the surgeon to use the cold/heat pack as a moldable positioning pack for an organ undergoing surgery.

The above objects, advantages and distinctions of the present invention, as well as the details of its construction, will become more apparent upon reference to the following description thereof with respect to the appended drawings and in which like numerals in the several views refer to corresponding parts. Before referring thereto, though, it is to be recognized that the description is not to be interpreted to be self-limiting but rather is representative only of the presently preferred embodiment.

DESCRIPTION OF THE PREFERRED EMBODIMENT

Figure 1:
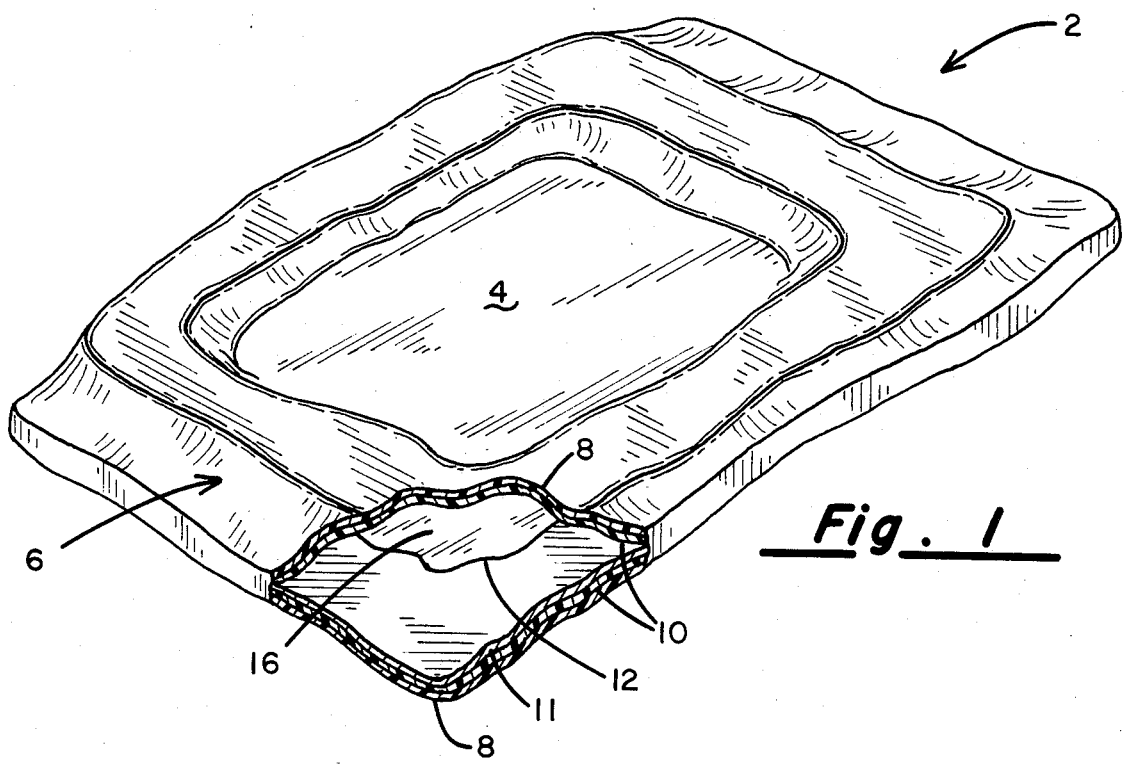
FIG. 1 shows in partial cutaway a perspective view of a typical cold/heat pack contemplated by the present invention.

Referring to FIG. 1, a cutaway perspective view is shown of the present cold/heat pack device 2 and which is shown as being formed in a rectangular pillow-like configuration. While bearing some outward resemblance to known cold packs, the present device includes a dough-like temperature storage medium which permits the molding of the cold/heat pack 2 into any number of shapes, depending upon the procedure, organ size or bodypart to be cooled or heated, space available, etc. Because the cold/heat pack 2 is used during various surgical procedures, it is also constructed with a variety of materials that are not adversely affected by autoclaving or other sterilizing procedures and which allow its use as a heat pack. The construction of the cold/heat pack 2 will be discussed in greater detail below. Because, too, of its intended predominant use as a cold pack, the following description will be principally directed thereto, but it is to be recognized that the same general principles apply for heating body parts.

Because of the desirability of keeping a body organ cool during many surgical procedures, such as cardiac surgery, and transportation, the cold/heat pack 2 of the present invention is constructed to be deformable, even at reduced temperatures, so as to permit the molding thereof into an appropriate shape before and during the time it is used. In this way, the cold/heat pack 2 can be made to conform to the shape of a body organ and thereby wrap-around more of the organ or body part and provide cooling to a larger surface area. As depicted in FIG. 1, the cold/heat pack 2 is shown with a centrally formed depression 4, but it is to be recognized that the specific shape of the depression 4 and/or the shape of the cold/heat pack 2 itself can be varied.

The moldability of the present cold/heat pack 2 is achieved in part via the construction of the container 6 from materials that are deformable and otherwise pliable over the temperature range of use. In this latter regard and because body tissue can be damaged from too cold or too hot a temperature, the cold/heat pack 2 is constructed to be used over temperatures in the range from 0° C. to 140° C. The lower temperatures are typically achieved by storing the cold/heat pack 2 in a freezer or the freezing compartment of a refrigerator, once it has been sterilized, to cool it to approximately −4° C.; whereas, the upper temperatures are attained by autoclaving.

The cold/heat pack 2 is further constructed so that when using it as a cold pack and upon molding and placing it in the body cavity, it absorbs only minimal radiant heat from the body cavity. This effect arises in part by partially shielding the organ in the depression 4, but also by constructing the container to reflect radiant heat, except in the area where the organ rests. Thus, only heat conducted by the organ is absorbed as the organ is cooled. It is also to be noted that the cold/heat pack 2 is insulated from the surface upon which it rests so as not to draw heat from that surface. By reflecting radiant body heat and by being insulated on its resting surface, the time over which cooling or heating is provided to the organ or body part is prolonged. Alternatively during heating, heat is not lost from the insulated side.

Referring now to the cutaway portion of the cold-/heat pack 2 shown in FIG. 1 and also to FIG. 2 which shows a detailed cross-sectional view taken along section lines 2—2 of FIG. 1, the constructional details of the cold/heat pack 2 will next be discussed. The container 6 is constructed as a multi-layered, air and moisture impervious envelope that is sealed after being filled with an appropriate temperature storage medium, yet to be described. Externally, the autoclavable container 6 may comprise a layer of silicon rubber, latex rubber 8, or other polymer film. Beneath the layer 8 is a polymer film layer 10 that includes a metal coated layer 11 over a portion thereof (i.e. the bottom for the cold/heat pack 2 of FIG. 1). The layers 10 and 11 remain flexible and pliable over the temperature range mentioned above. For example, the film layers 10 and 11 may comprise metal foil-coated Mylar film or a metal foil-coated polyethylene film.

Figure 2:
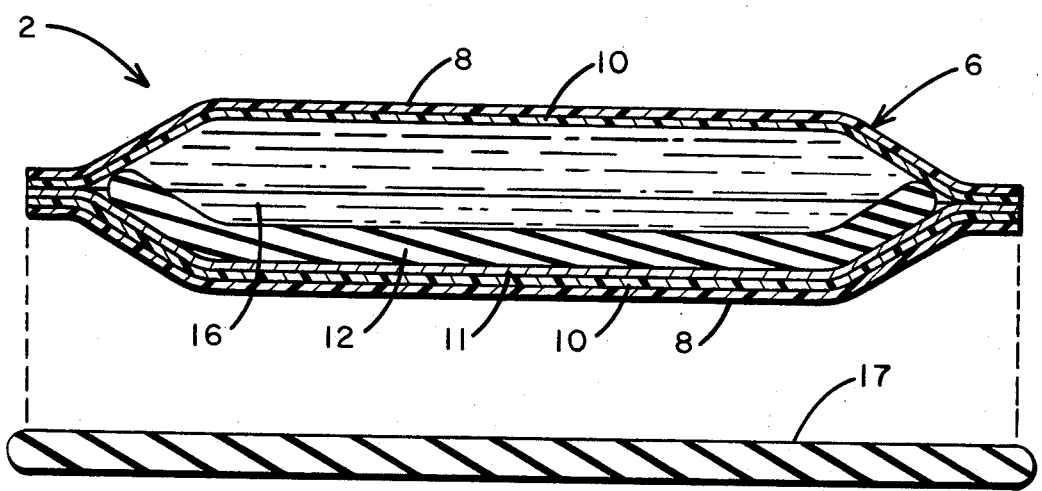
FIG. 2 shows a cross-section view of the cold/heat pack of FIG. 1.

Mounted interiorly over a portion of the container 6, and which in FIG. 2 is shown on the bottom, is a layer 12 of insulating material. In the one embodiment, the layer 12 comprises Thinsulate TM insulation which is manufactured by the 3M Company of St. Paul, Minnesota. The Thinsulate TM layer 12 is sealed within a polyethylene film envelope and the envelope is secured to the adjacent film layer 10 by a compatible adhesive. Alternatively, a number of layers of polyester, with or without sealing them in an envelope, might be used as the insulator 12. In combination, the layers 11 and 12 act to, respectively, reflect radiant heat from the body cavity and to insulate the surface upon which the cold/heat pack 2 rests against heat flow by conduction. This prolongs the cooling time of the moldable cold/heat pack 2 by minimizing the absorption of ambient heat and prevents excessive cooling or heating of adjacent tissue. As should also be apparent from the previously mentioned U.S. Pat. Nos. 3,736,769 and 4,457,308, the disclosed devices are not moldable, nor sterilizable, nor do they provide directional cooling or heating in a radiant heat reflecting, insulator containing, water and air impermeable package.

Before discussing the nature of the coolant or temperature storage medium 16 used in the present cold/heat pack 2, it is to be recognized that conventional construction techniques can readily be applied to the present structure. An exemplary fabrication sequence might comprise the construction of the insulation 12 containing envelope, which can be achieved by heat sealing the insulation 12 between two layers of polyethylene film. Similarly, the film layers 10 and the single metalic layer 11 can be sealed together by an appropriate adhesive to form an envelope with one open end and into which the insulator 12 can be inserted and attached. Upon filling the remaining open space with the temperature storage medium 16, the open end of the film layers 10 would be sealed. Thereafter, and assuming a sterile application, it is contemplated that the sealed envelope would be dip or spray coated with a latex rubber, silicon rubber 8 or other autoclavable coating. Alternatively, a separate molded rubber envelope could be made and then the coolant containing envelope could be inserted into this envelope and sealed.

Figure 3:
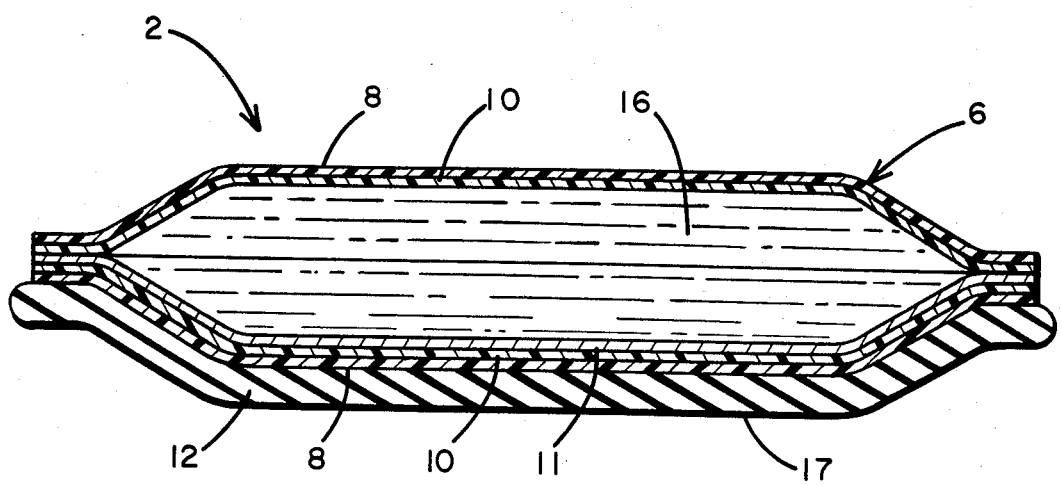
FIG. 3 shows a cross-sectional view through an alternative autoclavable embodiment of the present invention.

Attention is next directed to FIG. 3 wherein a cross-sectional view is shown of an alternative embodiment. Here, the insulation layer 12 is mounted externally to the cold/heat pack 2. Such a structure, however, is not as thermally desirable as that of FIG. 2 in that the insulator layer 12 is not incorporated into the container 6. It might also be mentioned that during use of the cold-/heat pack 2 of FIGS. 1 and 2 as a cold pack, a further insulative support pad 17 might be placed within the body cavity as shown in FIG. 2. The cold/heat pack 2 could then be placed on this pad 17 and thereby further prolong the useful life of the cold/heat pack 2.

Figure 4:
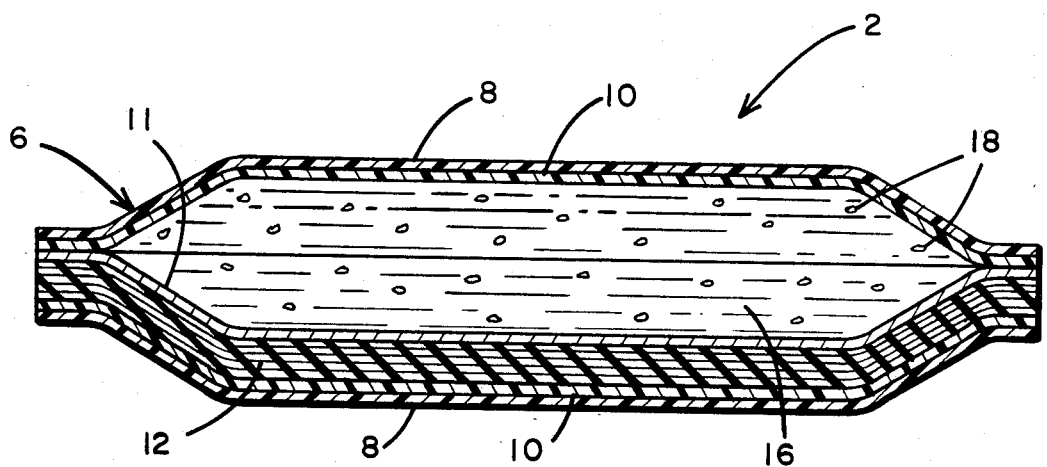
FIG. 4 shows a cross-sectional view through another alternative embodiment.

FIG. 4 shows yet another alternative embodiment in cross section and wherein the position of the insulator layer 12 and metal film layer 11 of FIG. 2 have been reversed. The insulator layer 12 is also now comprised of a number of polyester layers and the storage medium 16 includes metal or other temperature retaining particles 18.

Contained within the container 6 of the present cold/heat pack 2 is the temperature storage medium 16. It has been found that a mixture of de-ionized water, propylene glycol, and various polysaccharides and plant gums form an excellent storage material. In the proper proportions and after heating, such a mixture produces a pliable, dough-like storage medium which retains its pliability and moldability, over the previously mentioned temperature range, even after repeated sterilizations. Upon filling the container 6, the cold/heat pack 2 can thus be molded to a desired shape to conform to the organ being operated upon and thereby maximize the cooling surface area in contact with the organ. With the proper proportions, the medium 16 exhibits a rather sharp temperature threshold between pliability and a solid state at about $-17°$ C. This temperature should not be exceeded (in the negative direction) if tissue damage due to freezing is to be avoided. If, inadvertently, the cold/heat pack 2 is cooled to a point where the coolant 16 becomes a solid, the surgeon may knead it as he molds it to shape so as to raise its internal temperature slightly to the point where it is pliable or, alternatively, allow it to warm with the ambient room temperature, until it is moldable. This ensures a soft organ resting surface and prevents subjecting the organ to potentially harmful cold spots that might otherwise be formed with a rigid cold/heat pack 2.

In terms of its volume composition, the coolant 16, is principally comprised of de-ionized water. The next most prevalent ingredient is propylene glycol. Added then to these two constituents are any one or combination of a number of galacto mannans or polysacharrides, such as alginate, and various tree gums, (for example locus bean gum, gaur gum or xanthum gum) to control the viscosity and permit sterilization.

It is to be recognized that in the present mixture the galacto mannans act as a thickener or suspension agent. Each comprises a polysaccharide that is principally composed of three different types of repeating galatose and mannous subunits. When mixed in the proper proportions with water and propylene glycol, a dough-like substance is formed and the viscosity thereof can be adjusted by varying the proportions of each of the primary constituents. It is to be recognized, however, that alginate and other galacto-mannans alone do not accomodate sterilization, since upon heating, the heat causes the polysacharrides to turn to a syrup like consistancy. Any cold/heat pack of this type, as in U.S. Pat. No. 3,736,769, thus will not be moldable or retain its semi-solid shape after autoclaving.

Because a moldable, autoclavable temperature storage medium 16 is desired, the aforementioned gums are added and which when mixed in the proper proportions have been found to produce a stable moldable medium 16 that retains its pliability even after repeated sterilizations. For example, a typical coolant 16 composition may consist of 60 to 65 percent de-ionized water, 35 to 30 percent propylene glycol and the remainder alginate and locus bean gum. In particular, it has been found that the addition of 4 to 10 percent by volume of alginate with 1 to 2 percent locus beam gum produces moldable solids, while yet producing excellent heat stability to sterilization by autoclaving.

In this latter regard, the viscosity of the locus bean gum containing coolant can further be varied by (1) varying the concentration of locus bean gum in solution, (2) by varying the temperature applied during the mixing process and (3) by varying the amount of time at which the locus bean gum is held at a specific temperature during the mixing process. The addition of a gum material to the mixture thus facilitates the tailoring of the cold pack's viscosity characteristics during fabrication.

Further, by adjusting the proportions of the foregoing constituents, the temperature range over which the cold/heat pack 2 retains its moldability can be adjusted. Also, metal particle 18 or other heat or cold sink materials can be added that provide a high specific heat. In some applications it may also be desirable to prolong the time over which the storage medium 16 changes phases from its semi-solid state to a liquid form. In the present invention, the time over which this phase change takes place and for the temperature range mentioned can be prolonged by adding a quantity of one or more of several organic and inorganic chemicals to the medium 16. For example, some phase change chemicals that might be added are lithium chlorate, tetradecane, decanol, any C-15 through C-16 parafin, tetrahydrofuran or trimethylamine. In proper proportion, each of these chemicals delays the phase change within the medium 16. Thus, the cold/heat pack 2 retains the desired temperature for a longer time as it cools or heats. Caution should be exercised in selecting the phase change chemicals so that their toxic proporties are considered in light of the environment in which the cold pack is to be used.

Still other constituents that can be added to the medium 16 to prolong the period of its phase change are various known chemicals with reciprocal ions and which produce a reversible energy dependent reaction that involves the exchange of the base of one salt pair with the base of another salt pair. As heat is absorbed, it promotes the above reaction, rather than merely warming the storage medium 16, and thus stabilizes and prolongs the useful time of the cold/heat pack 2. One example of some reciprocal ion type chemicals are potassium fluoride and sodium carbonate. As should be apparent to those of skill in the art, however, the viscosity of the coolant 16 and the range of temperatures over which it remains dough-like may be adjusted by varying the concentration of each of the foregoing mentioned chemicals as well as by varying the temperature at which the mixture is prepared.

While the present invention has been described with respect to its presently preferred embodiment, it should be apparent to those of skill in the art that not only its constructional details might be varied, but also the concentrations of the temperature storage medium and which changes would still achieve a moldable, sterilizable and directional cold/heat pack. Accordingly, it is contemplated that the following claims should be interpreted so as to include all those equivalent embodiments within the spirit and scope thereof.

What is claimed is:

1. A moldable temperature transfer device comprising:

(a) an outer water impermeable skin defining a closed container;

(b) a temperature storage mixture enclosed within said container having a semi-solid dough like consistency over a range of temperatures at least as low as −17° C. and wherein said skin is flexibly deformed over said temperature range, said temperature storage mixture including a phase change prolonging material selected from the group consisting of lithium chlorate, tetradecane, decanol, C-15 through C-16 parafin, tetrahydrofuran and trimethylamine; and (c) a layer of heat insulating material disposed on a predetermined area of said skin.

2. The moldable device as in claim 1 wherein said mixture further includes an aqueous solution of propylene glycol and a galacto mannas selected from the group consisting of alginate, locus bean gum, gaur gum, xanthan gum and dextrands.

3. The moldable device as in claim 2 wherein said mixture further includes a quantity of heat or cold sinking particles.

4. A moldable device as in claim 3 wherein heat or cold sinking particles comprise a metallic particulate.

5. The moldable device as in claim 1 including a layer of radiant energy reflecting material mounted in predetermined relation to a portion of said skin.

6. The moldable device as in claim 1 constructed to be autoclavable.

7. The moldable device as in claim 1 wherein said skin is formed from silicon rubber.

8. The moldable device as in claim 1 wherein said skin is formed from a flexible polymer.

9. The moldable device as in claim 1 wherein said insulating material is mounted interiorly of said closed container.

10. The moldable device as in claim 1 including a layer of radiant energy reflecting material overlaying a predetermined portion of said skin within said container.

11. A moldable temperature transfer device comprising:

(a) a water impermeable polymer outer skin defining a closed container;

(b) a coolant mixture enclosed within said container comprising by volume approximately 55 to 65 percent de-ionized water, 25 to 35 percent propylene glycol, 4, to 10 percent galacto mannans selected from the group consisting of alginate and 1 to 2 percent plant gum selected from the group consisting of locus bean gum, gaur gum, xanthan gum and dextrands;

(c) layer of radiant energy reflecting material mounted adjacent to a predetermined portion of said skin; and (d) a layer of heat insulating material disposed in relation to a predetermined portion of said skin.

* * * * *